(12) United States Patent
Walak

(10) Patent No.: US 9,265,635 B2
(45) Date of Patent: Feb. 23, 2016

(54) STENT HAVING REMOVABLE ANCHORING ELEMENT

(71) Applicant: Boston Scientific Scimed, Inc., Maple Grove, MN (US)

(72) Inventor: Steven E. Walak, Natick, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 14/197,766

(22) Filed: Mar. 5, 2014

(65) Prior Publication Data

US 2014/0277560 A1 Sep. 18, 2014

Related U.S. Application Data

(60) Provisional application No. 61/783,308, filed on Mar. 14, 2013.

(51) Int. Cl.
*A61F 2/848* (2013.01)
*A61F 2/90* (2013.01)

(52) U.S. Cl.
CPC . *A61F 2/90* (2013.01); *A61F 2/848* (2013.01); *A61F 2002/8483* (2013.01); *A61F 2210/0076* (2013.01)

(58) Field of Classification Search
CPC .......................................................... A61F 2/82
USPC ........................................................ 623/1.14
See application file for complete search history.

(56) References Cited

U.S. PATENT DOCUMENTS

| | | | |
|---|---|---|---|
| 5,630,840 A | 5/1997 | Mayer | |
| 5,888,201 A | 3/1999 | Stinson et al. | |
| 8,114,147 B2 | 2/2012 | Wood et al. | |
| 8,303,669 B2 * | 11/2012 | Meade et al. | 623/23.65 |
| 8,628,583 B2 * | 1/2014 | Meade et al. | 623/23.64 |
| 2006/0276887 A1 | 12/2006 | Brady et al. | |
| 2008/0009934 A1 | 1/2008 | Schneider et al. | |
| 2011/0270405 A1 * | 11/2011 | Geitz et al. | 623/23.7 |
| 2012/0128793 A1 | 5/2012 | Miller et al. | |
| 2012/0184893 A1 * | 7/2012 | Thompson et al. | 604/9 |

* cited by examiner

*Primary Examiner* — Thomas J Sweet
*Assistant Examiner* — Wade P Schutte
(74) *Attorney, Agent, or Firm* — Seager, Tufte & Wickhem, LLP

(57) ABSTRACT

A stent comprising a radially expandable elongate tubular support structure, the elongate tubular support structure comprising an inner surface and an outer surface and an anchoring element disposed on at least a portion of the outer surface of the tubular support structure, the anchoring element is separate and removable from the elongate tubular support structure.

18 Claims, 6 Drawing Sheets

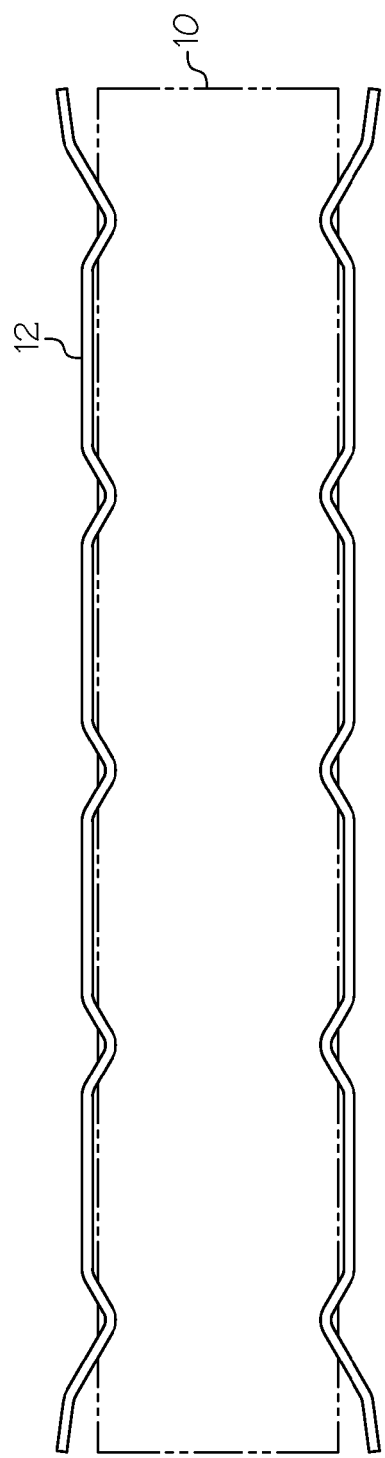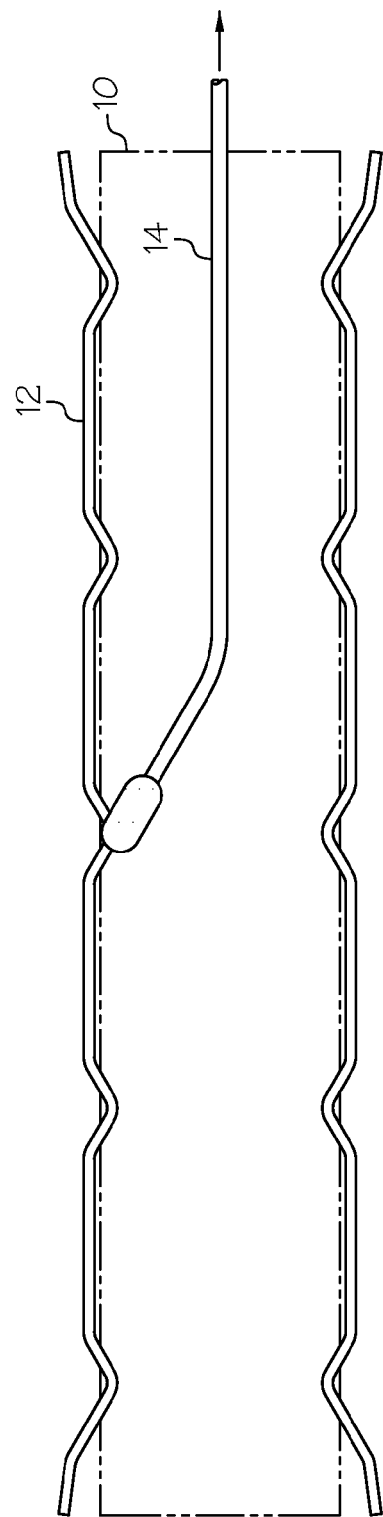

STENT HAVING REMOVABLE ANCHORING ELEMENT

CROSS-REFERENCE TO RELATED APPLICATIONS

This application claims priority to U.S. Patent Provisional Application No. 61/783,308, filed Mar. 14, 2013, the entire contents of which are hereby incorporated herein by reference.

BACKGROUND OF THE INVENTION

Medical prostheses frequently referred to as stents are well known and commercially available. These devices are used within body vessels of humans for a variety of medical applications. Examples include intravascular stents for treating stenoses, stents for maintaining openings in the urinary biliary, tracheobronchial, esophageal, and renal tracts, and vena cava filters. Stents may also be used by physicians for malignant tumors. Benign tumors are seldom stented with metal platforms.

Typically, a stent is delivered into position at a treatment site in a compressed state using a delivery device. After the stent is positioned at the treatment site, the delivery device is actuated to release the stent. Following release of the stent, self-expanding stents are allowed to self-expand within the body vessel. Alternatively, a balloon may be used to expand other types of stents. This expansion of the stent in the body vessel helps to retain the stent in place and prevent movement or migration of the stent. Stents are typically composed of stent filaments.

Stents may be categorized as permanent, removable or bioresorbable. Permanent stents are retained in place and incorporated into the vessel wall. Removable stents are removed from the body vessel when the stent is no longer needed. A bioresorbable stent may be composed of, or include, biodegradable material or bioresorbable material which is broken down by the body and absorbed or passed from the body when it is no longer needed.

Commonly used materials for known stent filaments include Elgiloy® and Phynox® metal spring alloys. Other metallic materials that may be used for stents filaments are 316 stainless steel, MP35N alloy and superelastic Nitinol nickel-titanium alloy. Another stent, available from Schneider (USA) Inc. of Minneapolis, Minn., has a radiopaque clad composite structure such as shown in U.S. Pat. No. 5,630,840 to Mayer. Stents can also be made of a titanium alloy as described in U.S. Pat. No. 5,888,201.

Bioabsorbable implantable endoprostheses such as stents, stent-grafts, grafts, filters, occlusive devices, and valves may be made of poly(alpha-hydroxy acid) such as poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester, poly(aminoacides), or related copolymers materials, each of which have a characteristic degradation rate in the body. For example, PGA and polydioxanone are relatively fast-bioabsorbing materials (weeks to months) and PLA and polycaprolactone are a relatively slow-bioabsorbing material (months to years).

Stents may also be covered with various materials to encourage or inhibit tissue attachment to the stent. Covered stents are gaining, favor for biliary applications because they more effectively inhibit tissue attachment, intrusion, and constriction of the tract than bare stents. For example, polytetrafluoroethylene (PTFE) covered stents are desirable for removable stents because tissue attachment or in-growth is reduced in comparison to bare stent or a stent covered with textile (polyester) material. Laminated ePTFE may also be used to cover stents.

As stents are covered with material to aid in their removal, the possibility of stent migration from the treatment site increases. There remains a continuing need for covered stents which include characteristics to maintain the stent in position at the treatment site.

Stents are also particularly susceptible to migration when used in certain parts of the body such as the esophageal tract.

One solution to stent migration is to add anchors or barbs to the stent. However, the use of stent anchors to prevent stent migration is also problematic, as such anchors generally permit tissue in-growth into the stent, thereby preventing stent migration, but at the same time making removal and/or repositioning of the stent difficult or dangerous.

There remains a need in the art for an improved stent that is resistant to migration.

SUMMARY OF THE INVENTION

In one embodiment, the present invention relates to a stent comprising a radially expandable elongate tubular support structure, the elongate tubular support structure comprising an inner surface and an outer surface and an anchoring element disposed on at least a portion of the outer surface of the tubular support structure, the anchoring element is separate and removable from the elongate tubular support structure.

In another embodiment, the present invention relates to a stent comprising a radially expandable elongate tubular support structure, the elongate tubular support structure comprising a braided or woven open network of fibers or filaments and an anchoring element interwoven with the braided or woven open network, the anchoring element is separate and removable from said elongate tubular support structure.

In alternative embodiments, the present invention relates a stent comprising a radially expandable elongate tubular support structure, the elongate tubular support structure comprising an inner surface and an outer surface and an anchoring element disposed on said at least a portion of said outer surface of said tubular support structure, the anchoring element is separate and removable from said elongate tubular support structure, the anchoring element is in the shape of a nail or staple, the nail or staple is positioned on the stent after the stent has been deployed in the lumen of a patient.

BRIEF DESCRIPTION OF THE DRAWINGS

FIG. 1 is a side view of a stent having a removable anchor element incorporated thereon.

FIG. 2 is a side view of a stent similar to that in FIG. 1 in combination with a removal tool for removing the removable anchor element from the patient's body.

Figure 3:
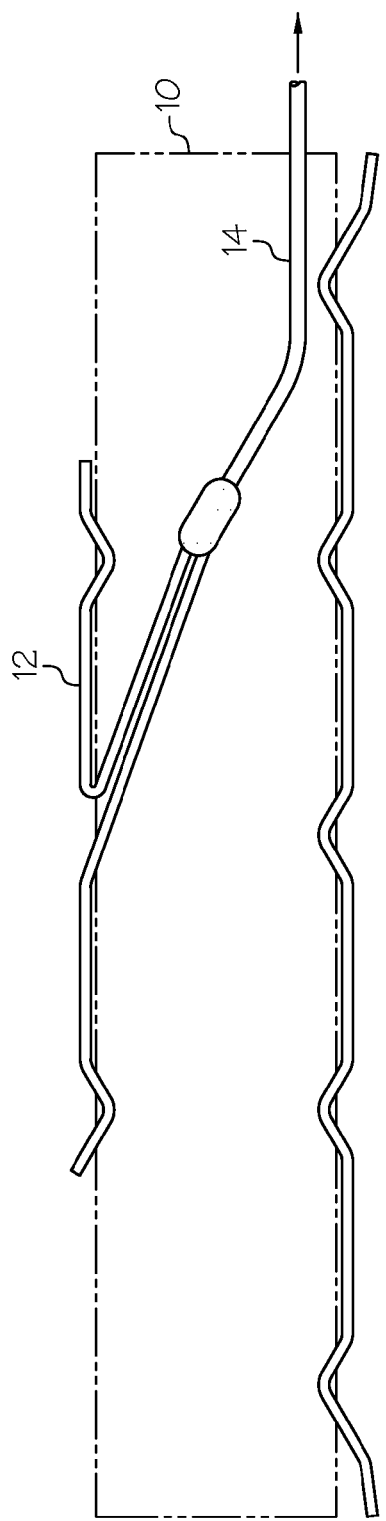
FIG. 3 is a side view of the stent and removal tool similar to that shown in claim 2 with the removable anchor being partially removed from the stent.

These and other aspects, embodiments and advantages of the present disclosure will become immediately apparent to those of ordinary skill in the art upon review of the Detailed Description and Claims to follow.

DETAILED DESCRIPTION OF THE INVENTION

While this invention may be embodied in many forms, there are described in detail herein, specific embodiments of the present disclosure. This description is an exemplification of the principles of the present disclosure and is not intended to limit the disclosure to the particular embodiments illustrated herein.

Turning now to the figures, FIG. 1 illustrates one embodiment of a stent support structure 10 having a removable anchoring element 12 disposed thereon. Any number of methods can be employed to removably attach the removable anchoring element to the stent 10. The removable anchoring element 12 provides robust attachment of the stent 10 to the body organ targeted for treatment. The removable anchoring element 12 is designed to be readily removed from the stent 10 prior to removal of the stent 10 from the patient's body. In some embodiments, the removable anchoring element is therefore separate from and in contact with but unattached to the stent 10.

The anchoring element may be temporarily attached by alternative mechanical means such as clips, springs or interlocking features which may be disengaged and removed by the physician. Attachment of the anchoring element may be facilitated by the use of temporary adhesive or structures that degrade with exposure to the bodies environment.

In one particular embodiment shown in FIG. 2, removable anchoring element 12 is in the form of a wire which may be round or flat. In some embodiments a flat wire has been found to be beneficial because its low profile cross section requires less space in the reduced diameter stent delivery device configuration. Stent 10 may be coiled or patterned as a braided or woven open network of wires, fibers or filaments interwoven in a braided pattern to form a tubular stent 10, as disclosed, for example, in commonly assigned U.S. Patent Publication No. 2012/0128793, the entire content of which is incorporated by reference herein. Similar stent constructions are also disclosed in commonly assigned U.S. Patent Publication Nos. 2006/0276887 and 2008/0009934, each of which is incorporated by reference herein in its entirety. The stent may also be fabricated from a cut metal tube such as a slotted tube or tubes formed with serpentine structures of straight and curved strut configurations such as those made for vascular applications. These stents can be made of stainless steel, nitinol, cobalt-chromium alloys or other materials known in the art and then laser cut into the desired stent geometry.

In this embodiment, the removable anchoring element 12 may extend in the direction of the longitudinal axis of the stent and can be interwoven in the braided construction of the stent 10.

Wires extending in the longitudinal direction of the stent 10 are advantageous in that they require less space when the stent is compressed and allow for smaller delivery system diameters than wires having a circumferential component.

Any number of wires can be employed. Suitably, a minimum of two wires are positioned symmetrically about the circumference of the stent 10 to provide uniform anchoring in a body vessel. The lumen wall anchor points may be located not only at the middle or end portions of the stent, but at any other portion of the stent as well. However, any number of wires may be employed such as 3, 4, 5, 6 and so forth.

Additionally, a single circumferential ring of anchoring elements may be positioned in the middle of the stent to prevent stent "walking" which may occur if anchoring elements are positioned at both ends of the stent.

Figure 8:
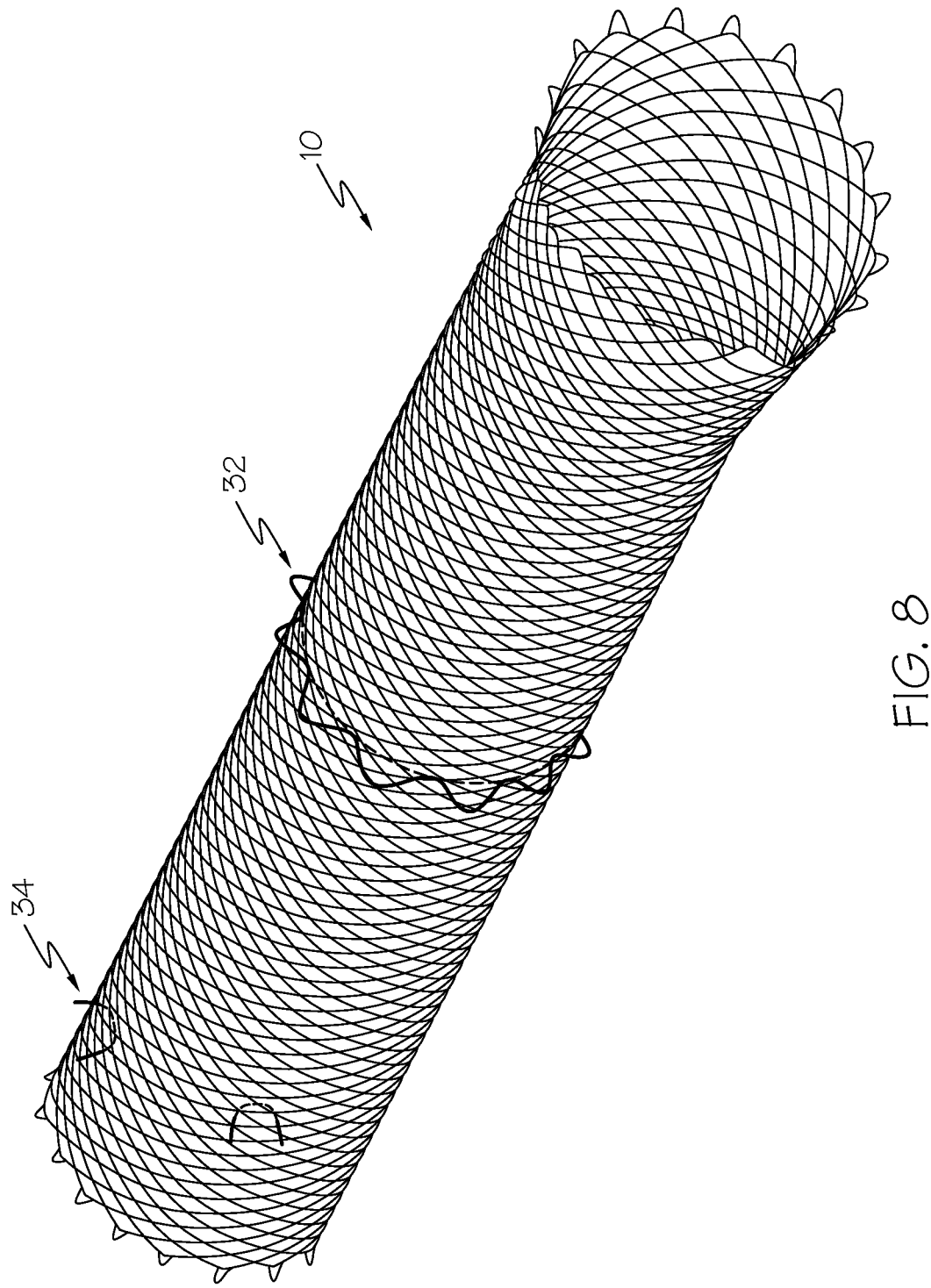
FIG. 8 is a perspective view of a stent illustrating alternative embodiments of temporary anchoring elements.

FIG. 8 is representative of alternative embodiments wherein stent 10 has a temporary anchor 32 that is "pre-attached" to the stent in the form of a circumferential anchor 32. Alternatively, a temporary anchor 34 in the form of staples or nails may be disposed on stent 10 after stent 10 has been deployed in the body at the treatment site. The staples 34 can be removed when it is desirable to remove stent 10 from the body. In some embodiments, the nails or staples 34 are disposed on the proximal end of the stent. However, the nails or staples can be disposed on the center portion, the distal portion, or any combination of the three portions as well. The circumferential anchor 32 and the staples or nails 34 can be employed in separate embodiments of stent 10, rather than in combination as shown in FIG. 8.

Moreover, the temporary anchor 34 or the nails or staples 34 shown in FIG. 8 on a stent having a flared proximal end, can be employed on any other stent configuration as well.

The removable anchoring element 12 may be constructed such that the ends of the wire are positioned at the ends of the stent 10. However, the removable anchoring element 12 may be constructed such that the ends of the wire are positioned at any portion of the stent 10 where anchoring is needed.

Stent can be formed from any suitable stent material including, but not limited to, shape memory metals such as Nitinol, cobalt-chromium alloys such as Elgiloy® or L605, stainless steel, nickel, titanium, polymers, shape memory polymers, etc.

The removable anchoring element 12 can similarly be made of any suitable stent material including, but not limited to, shape memory metals such as Nitinol, cobalt-chromium alloy such as Elgiloy or Alloy L605, stainless steel, nickel, titanium, polymers, shape memory polymers, etc.

In one particular embodiment, nitinol wires are woven into the braided structure of the stent 10 in a longitudinal pattern.

Alternatively, stainless steel has been found to be beneficial where increased stiffness when smaller volumes are desired.

Figure 4:
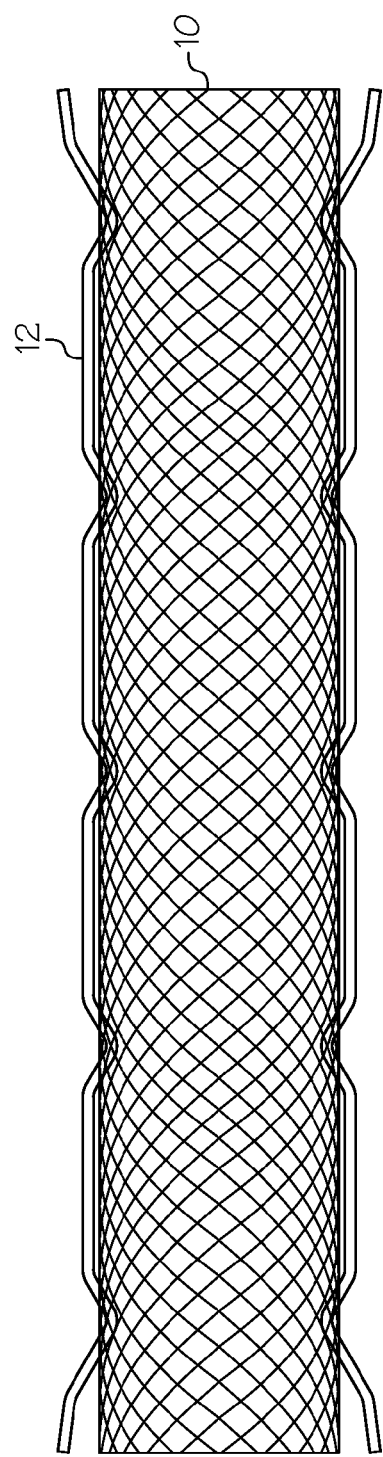
FIG. 4 is a side view of a generic woven stent having a removable anchor element interwoven in the braided pattern of the stent.

In one embodiment as shown in FIGS. 3 and 4, a removal tool 14, such as rat tooth retrieval forceps, a snare or a basket can be used to grasp the removable anchor element 12 and pull it in the proximal direction of the stent 10 to remove it from the patient's body. Specially designed tools to locate and withdraw the temporary anchor may also be envisioned. In this embodiment, the removable anchor element 12 is grasped by removal tool 14 in the central portion of the stent and at approximately the middle portion of the removable anchor element 12.

In one embodiment, the anchoring element 12 is designed to fold in the middle such as by reducing the amount of material or by providing a strain relief such as by scoring or providing depressions or grooves in the wire to allow the middle portion to bend more readily.

Reducing material in the middle of the wire can be done using any suitable method known in the art such as by laser etching, grinding, and so forth.

In alternative embodiments, the removable anchor element can be formed from polymers or metal alloys such as magnesium, which degrade in vivo at a predetermined rate allowing stent removal after a set time.

Degradable or biodegradable materials are those which break down and lose their structural integrity in vivo. Examples of suitable biodegradable polymers include, but are not limited to, poly(amides) such as poly(amino acids) and poly(peptides), poly(esters) such as polylactide including poly(DL-lactide) and polyglycolide, and copolymers thereof such as polylactide-co-glycolide including poly(DL-lactide-co-glycolide), poly(L-lactide-co-glycolide), poly(caprolactone) and polylactide-co-caprolactone including poly(DL-lactide-co-caprolactone and poly(L-lactide-co-caprolactone), poly(anhydrides), poly(orthoesters), poly(carbonates) including tyrosine derived polycarbonates, polyhydroxyvalerate, polyhydroxybutyrate, polyhydroxybutyrate-co-valerate, and chemical derivatives thereof (substitutions, additions of chemical groups, for example, alkyl, alkylene, hydroxylations, oxidations, and other modifications routinely made by those skilled in the art), copolymers and mixtures thereof.

The removable anchor element 12 can be employed with any stent construction.

Figure 5:
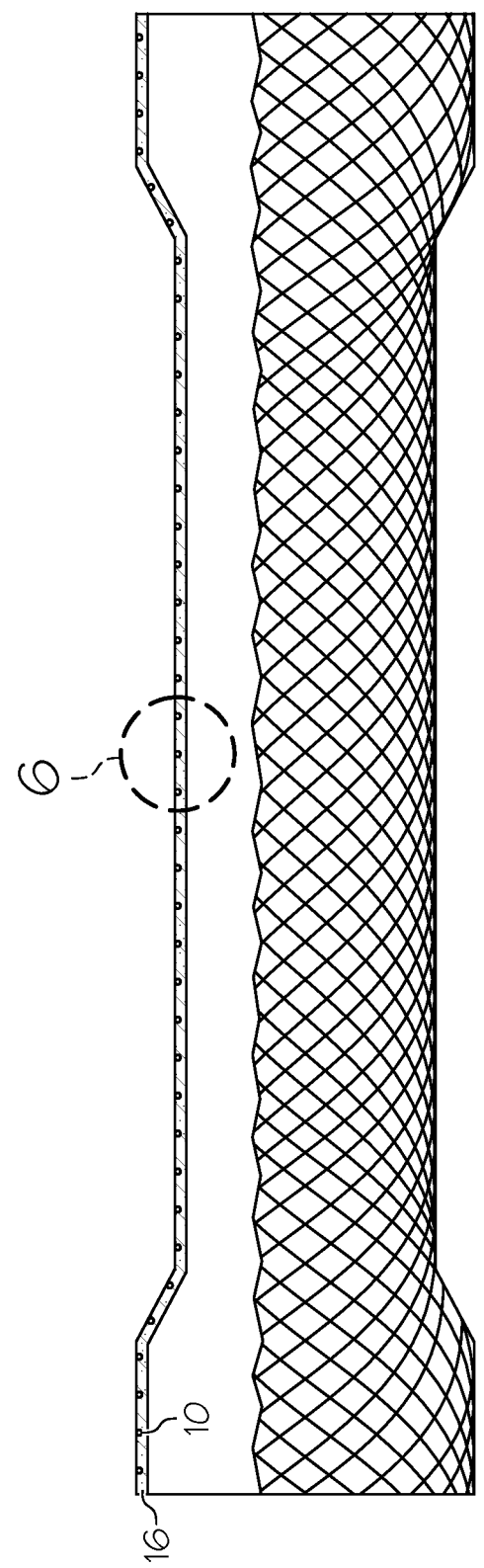
FIG. 5 is a side view of a covered stent wherein the covering is disposed on the inner surface of the stent.
Figure 6:
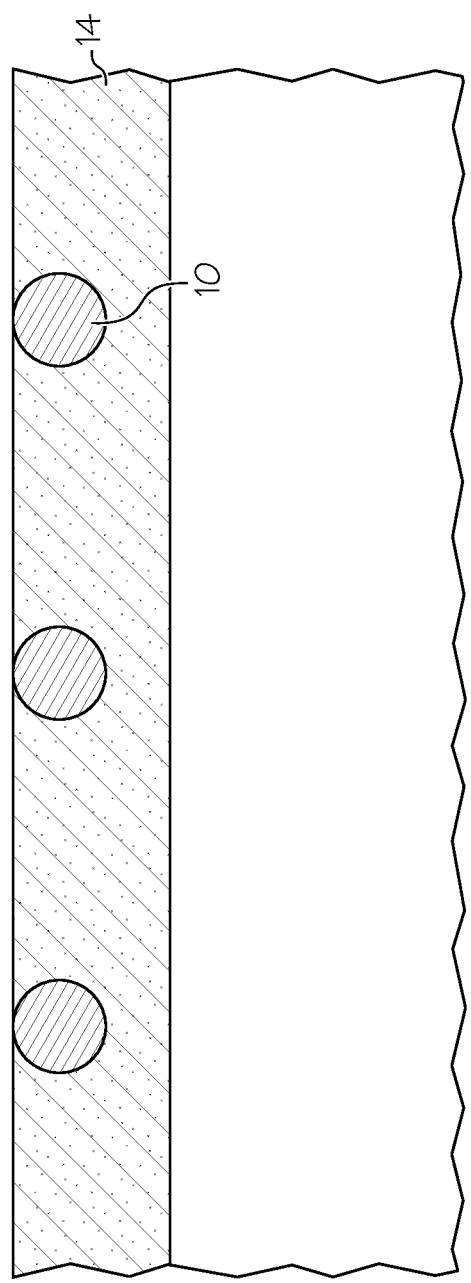
FIG. 6 is taken at section 6 is FIG. 5 and is an enlarged view of the stent wall illustrating the stent embedded in the covering material.

One particular example is shown in FIGS. 5 and 6. In this embodiment, stent 10 is a self-expanding stent formed of a shape memory metal such as nitinol having a silicone covering. The stent has a braided wire construction. In this embodiment, stent 10 is shown having a silicone covering 12. Stent 10 is disposed on silicone covering 12 and is partially embedded therein. FIG. 2 is a partial cross-sectional view of the stent taken at section 2 in FIG. 1. Covered stents of this type are described in commonly assigned US Patent Publication Nos. 2006/0276887 and 2008/0009934, each of which is incorporated by reference herein in its entirety.

Any stent can have a covering and the coverings are thus not limited to nitinol stents. Moreover, the stent need not be covered whatsoever, may be partially covered or may be fully covered. The stent may also have a covering on the inside, the outside or both.

Other suitable covering materials can be employed as well. Examples of other suitable covering materials include, but are not limited to, polyethylene, polypropylene, polyvinyl chloride, polytetrafluoroethylene, including expanded polytetrafluoroethylene (ePTFE), fluorinated ethylene propylene, fluorinated ethylene propylene, polyvinyl acetate, polystyrene, poly(ethylene terephthalate), naphthalene, dicarboxylate derivatives, such as polyethylene naphthalate, polybutylene naphthalate, polytrimethylene naphthalate and trimethylenediol naphthalate, polyurethane, polyurea, polyamides, polyimides, polycarbonates, polyaldehydes, polyether ether ketone, natural rubbers, polyester copolymers, styrene-butadiene copolymers, polyethers, such as fully or partially halogenated polyethers, and copolymers and combinations thereof. See, for example, commonly assigned U.S. Pat. No. 8,114,147, the entire content of which is incorporated by reference herein.

Figure 7:
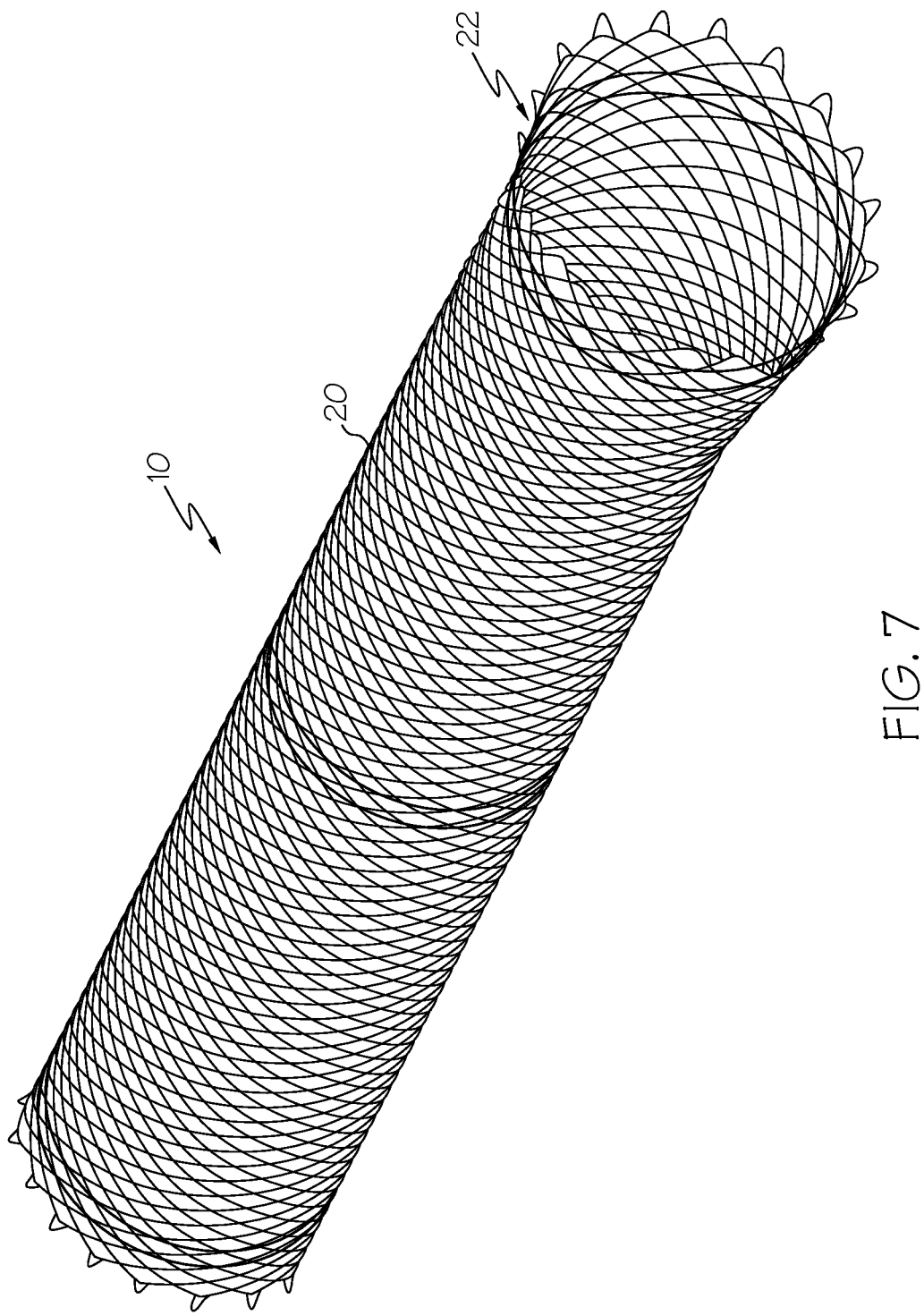
FIG. 7 is a perspective view of an alternative embodiment of a woven or braided stent having a flared proximal end.

Alternatively, stent 10 may have a braided construction with a flared proximal end 22 as shown in FIG. 7. In this embodiment, stent 10 is an esophageal stent. Stent 10 may be formed of any suitable stent material including metallic and non-metallic materials as well as shape memory materials. Examples of suitable materials include, but are not limited to, shape memory alloys such as Nitinol, other metallic materials such as stainless steel, tantalum, titanium, nickel-chrome, or cobalt-chromium alloys such as those sold under the tradename of Elgiloy®. Stent 10 may have a flared distal end or flared proximal and distal ends as well.

Therapeutic agents may also be incorporated into the stent structure as is known in the art.

The removable anchor element can be employed herein with any stent and is suitably employed with temporary stents which are removed from the patient's body after some specified period of time.

The description provided herein is not to be limited in scope by the specific embodiments described which are intended as single illustrations of individual aspects of certain embodiments. The methods, compositions and devices described herein can comprise any feature described herein either alone or in combination with any other feature(s) described herein. Indeed, various modifications, in addition to those shown and described herein, will become apparent to those skilled in the art from the foregoing description and accompanying drawings using no more than routine experimentation. Such modifications and equivalents are intended to fall within the scope of the appended claims.

All publications, patents and patent applications mentioned in this specification are herein incorporated by reference in their entirety into the specification to the same extent as if each individual publication, patent or patent application was specifically and individually indicated to be incorporated herein by reference. Citation or discussion of a reference herein shall not be construed as an admission that such is prior art.

The invention claimed is:

1. A stent, the stent comprising:
    a radially expandable elongate tubular support structure, the elongate tubular support structure comprising an inner surface and an outer surface; and
    an anchoring element disposed on at least a portion of said outer surface of said tubular support structure, the anchoring element is separate and removable from said elongate tubular support structure, the tubular support structure comprising a braided, woven or knit structure, and the anchoring element is woven into and out of the braided, woven or knit structure such that the anchoring element enters, exits, and then re-enters adjacent fibers of the braided, woven or knit structure.

2. The stent of claim 1 wherein said anchoring element enters, exits, and then re-enters said braided, woven or knit structure in a longitudinal direction with the tubular support structure.

3. The stent of claim 1 wherein said stent comprises a partial or full covering.

4. The stent of claim 2 wherein said covering comprises silicone.

5. The stent of claim 2 wherein said stent covering is on the inner surface of the tubular support structure.

6. The stent of claim 1 wherein said anchoring element is in the form of a flat or a round wire.

7. The stent of claim 1 wherein said anchoring element is nitinol or stainless steel.

8. The stent of claim 6 wherein said anchoring element is a magnesium alloy.

9. The stent of claim 1 wherein said stent is an endoscopic stent.

10. The stent of claim 9 wherein said stent comprises a member selected from the group consisting of esophageal stents, pancreatic stents, duodenal stents, colonic stents, biliary stents and airway stents.

11. A stent, the stent comprising:
    a radially expandable elongate tubular support structure, the elongate tubular support structure comprising a braided or woven open network of fibers or filaments;
    an anchoring element woven into and out of said braided or woven open network such that the anchoring element enters, exits, and then re-enters adjacent fibers of said braided or woven open network, the anchoring element is separate and removable from said elongate tubular support structure.

12. The stent of claim 11 wherein said anchoring element enters, exits, and then re-enters said braided or open network in a longitudinal direction with the tubular support structure.

13. The stent of claim 11 wherein said anchoring element is in the form of a flat or round wire.

14. The stent of claim 13 wherein said anchoring element is a flat wire.

15. The stent of claim 13 wherein said anchoring element is nitinol or stainless steel.

16. The stent of claim 13 wherein said anchoring element is a magnesium alloy.

17. The stent of claim 11 further comprising a partial or full covering.

18. The stent of claim 11 wherein said stent is an endoscopic stent.

* * * * *